(12) United States Patent
Indo et al.

(10) Patent No.: US 10,794,890 B2
(45) Date of Patent: Oct. 6, 2020

(54) METHOD OF OBTAINING ASPHALTENE CONTENT OF CRUDE OILS

(71) Applicant: Schlumberger Technology Corporation, Sugar Land, TX (US)

(72) Inventors: Kentaro Indo, Sugar Land, TX (US); Kai Hsu, Sugar Land, TX (US); Julian Pop, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 1226 days.

(21) Appl. No.: 14/135,377

(22) Filed: Dec. 19, 2013

(65) Prior Publication Data

US 2015/0176407 A1    Jun. 25, 2015

(51) Int. Cl.
| | | |
|---|---|---|
| *E21B 49/08* | (2006.01) | |
| *G01N 33/28* | (2006.01) | |
| *G01N 21/31* | (2006.01) | |
| *G01V 8/00* | (2006.01) | |
| *G01V 8/12* | (2006.01) | |
| *G01N 21/85* | (2006.01) | |
| *G01N 21/53* | (2006.01) | |
| *G01N 21/59* | (2006.01) | |
| *G01N 21/3577* | (2014.01) | |

(52) U.S. Cl.
CPC ....... *G01N 33/2823* (2013.01); *E21B 49/082* (2013.01); *G01N 21/31* (2013.01); *G01N 21/534* (2013.01); *G01N 21/59* (2013.01); *G01N 21/85* (2013.01); *G01V 8/00* (2013.01); *G01V 8/12* (2013.01); *E21B 49/0875* (2020.05); *G01N 21/3577* (2013.01)

(58) Field of Classification Search
CPC ...... G01N 33/2823; G01N 21/31; G01V 8/12; G01V 8/00; E21B 49/082; E21B 2049/085
See application file for complete search history.

(56) References Cited

U.S. PATENT DOCUMENTS

| | | | |
|---|---|---|---|
| 4,843,247 A | 6/1989 | Yamazoe et al. | |
| 7,996,154 B2 * | 8/2011 | Zuo | E21B 47/102 |
| | | | 175/40 |

(Continued)

FOREIGN PATENT DOCUMENTS

| | | |
|---|---|---|
| GB | 2458551 A | 9/2009 |
| WO | WO2011007268 A1 | 1/2011 |

(Continued)

OTHER PUBLICATIONS

U.S. Appl. No. 13/913,462, filed Jun. 9, 2013.

(Continued)

*Primary Examiner* — Mohamed Charioui
*Assistant Examiner* — Jeremy A Delozier

(57) ABSTRACT

A method for measuring asphaltene content of a crude oil is provided. In one embodiment, the method includes measuring an optical density of a live crude oil within a well and calculating a formation volume factor of the live crude oil based on the measured optical density. The method also includes determining asphaltene content of the live crude oil based on the measured optical density and the calculated formation volume factor of the live crude oil. Additional methods, systems, and devices are also disclosed.

20 Claims, 7 Drawing Sheets

(56) References Cited

U.S. PATENT DOCUMENTS

| | | | |
|---|---|---|---|
| 8,269,961 B2* | 9/2012 | Mostowfi | G01N 33/2823 |
| | | | 356/246 |
| 2003/0176973 A1* | 9/2003 | Hashem | E21B 49/08 |
| | | | 702/13 |
| 2005/0007583 A1* | 1/2005 | DiFoggio | G01V 8/02 |
| | | | 356/301 |
| 2008/0156088 A1* | 7/2008 | Hsu | E21B 49/10 |
| | | | 73/152.23 |
| 2008/0173445 A1 | 7/2008 | Dong et al. | |
| 2011/0088895 A1 | 4/2011 | Pop et al. | |
| 2013/0118734 A1 | 5/2013 | Csutak | |
| 2014/0096955 A1 | 4/2014 | Indo et al. | |
| 2014/0150545 A1 | 6/2014 | Hsu et al. | |
| 2014/0360257 A1 | 12/2014 | Hsu et al. | |
| 2015/0204189 A1 | 7/2015 | Indo et al. | |

FOREIGN PATENT DOCUMENTS

| WO | 2013109716 A1 | 7/2013 | |
|---|---|---|---|
| WO | WO 2013109716 A1 * | 7/2013 | ............ E21B 49/00 |

OTHER PUBLICATIONS

U.S. Appl. No. 13/693,782, filed Dec. 4, 2012.
U.S. Appl. No. 13/644,772, filed Oct. 4, 2012.
U.S. Appl. No. 61/666,593, filed Jun. 29, 2012.
Aske et al., Determination of Saturate, Aromatics, Resin, and Asphaltene (SARA) Components in Crude Oils by Means of Infrared and Near-Infrared Spectroscopy, Energy and Fuels, 2001, vol. 15, No. 5, pp. 1304-1312.
Kharrat, et al. "Asphaltene Content Measurement Using an Optical Spectroscopy Technique," Energy and Fuels, 2013, vol. 27, No. 5, pp. 2452-2457.
International Search Report and Written Opinion issued in PCT/US2014/071036 dated Mar. 24, 2015, 9 pages.
International Preliminary Report on Patentability issued in PCT/US2014/071036 dated Jun. 21, 2016. 5 pages.
Extended Search Report R. 62 and Examination Report issued in European Patent Application 14871771.3 dated Jul. 28, 2017. 8 pages.

* cited by examiner

METHOD OF OBTAINING ASPHALTENE CONTENT OF CRUDE OILS

BACKGROUND

Wells are generally drilled into subsurface rocks to access fluids, such as hydrocarbons, stored in subterranean formations. The formations penetrated by a well can be evaluated for various purposes, including for identifying hydrocarbon reservoirs within the formations. During drilling operations, one or more drilling tools in a drill string may be used to test or sample the formations. Following removal of the drill string, a wireline tool may also be run into the well to test or sample the formations. These drilling tools and wireline tools, as well as other wellbore tools conveyed on coiled tubing, drill pipe, casing or other means of conveyance, are also referred to herein as "downhole tools." Certain downhole tools may include two or more integrated collar assemblies, each for performing a separate function, and a downhole tool may be employed alone or in combination with other downhole tools in a downhole tool string.

Formation evaluation may involve drawing fluid from the formation into a downhole tool. In some instances, the fluid drawn from the formation is retained within the downhole tool for later testing outside of the well. In other instances, downhole fluid analysis may be used to test the fluid while it remains in the well. Such analysis can be used to provide information on certain fluid properties in real time without the delay associated with returning fluid samples to the surface.

Asphaltenes are generally the heaviest fraction and the most polar component in a petroleum mixture. Asphaltenes are insoluble in n-alkanes and soluble in toluene. They can be precipitated as solid particles under certain pressure and temperature conditions in some crude oils or by injecting a solvent. Asphaltene deposition can sometimes negatively impact hydrocarbon production, such as by plugging pipelines and impairing the flow of hydrocarbons through formations and into wells. Various techniques are known for measuring the asphaltene content of stock tank oil (STO), which is oil at surface conditions (e.g., 60° F. and 14.7 psia) following bubbling of gaseous components out of the oil.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In one embodiment of the present disclosure, a method includes measuring an optical density of a live crude oil within a well. The method further includes calculating a formation volume factor of the live crude oil based on the measured optical density and then determining asphaltene content of the live crude oil based on the measured optical density and the calculated formation volume factor of the live crude oil.

In another embodiment, a method includes routing a fluid into a downhole tool with a spectrometer having an emitter and a detector. The method also includes irradiating the fluid in the downhole tool with electromagnetic radiation from the emitter and detecting a portion of the electromagnetic radiation that is transmitted through the fluid with the detector. An optical density of the fluid may then be determined based on the detected portion of the electromagnetic radiation transmitted through the fluid. In turn, an asphaltene content of the fluid can then be determined using the optical density.

In a further embodiment, an apparatus includes a downhole sampling tool and a controller. The downhole sampling tool includes an intake for receiving a formation fluid and a downhole fluid analysis module that permits measurement of an optical density of the received formation fluid. The controller can be operated to determine asphaltene content of the received formation fluid using the optical density of the received formation fluid and a formation volume factor of the received formation fluid.

Various refinements of the features noted above may exist in relation to various aspects of the present embodiments. Further features may also be incorporated in these various aspects as well. These refinements and additional features may exist individually or in any combination. For instance, various features discussed below in relation to the illustrated embodiments may be incorporated into any of the above-described aspects of the present disclosure alone or in any combination. Again, the brief summary presented above is intended just to familiarize the reader with certain aspects and contexts of some embodiments without limitation to the claimed subject matter.

BRIEF DESCRIPTION OF THE DRAWINGS

These and other features, aspects, and advantages of certain embodiments will become better understood when the following detailed description is read with reference to the accompanying drawings in which like characters represent like parts throughout the drawings, wherein.

DETAILED DESCRIPTION OF SPECIFIC EMBODIMENTS

It is to be understood that the present disclosure provides many different embodiments, or examples, for implementing different features of various embodiments. Specific examples of components and arrangements are described below for purposes of explanation and to simplify the present disclosure. These are, of course, merely examples and are not intended to be limiting.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not mandate any particular orientation of the components.

The present disclosure relates to using optical spectrometry data to determine asphaltene content of a fluid. More particularly, some embodiments of the present disclosure relate to using downhole optical spectrometry data to determine asphaltene content of live crude oils within wells. In this manner, the asphaltene content of downhole crude oils can be obtained in situ, even in the presence of gas within these crude oils. As described in detail below, in some embodiments the asphaltene content of a fluid is determined based on one or more optical densities of the fluid and a formation volume factor.

Figure 1:
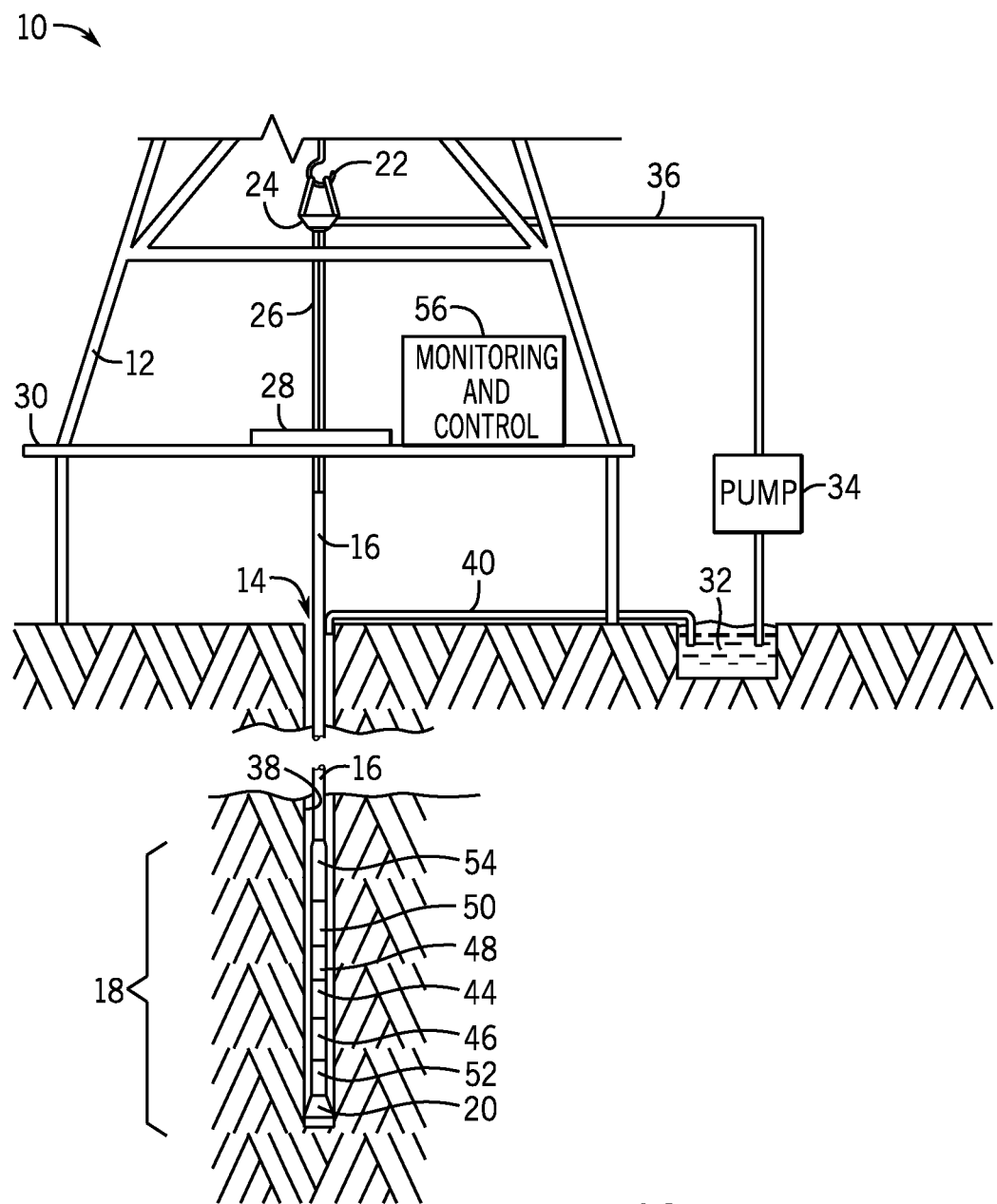
FIG. 1 generally depicts a drilling system having a fluid sampling tool in a drill string in accordance with one embodiment of the present disclosure.

Turning now to the drawings, a drilling system 10 is depicted in FIG. 1 in accordance with one embodiment. While certain elements of the drilling system 10 are depicted in this figure and generally discussed below, it will be appreciated that the drilling system 10 may include other components in addition to, or in place of, those presently illustrated and discussed. As depicted, the system 10 includes a drilling rig 12 positioned over a well 14. Although depicted as an onshore drilling system 10, it is noted that the drilling system could instead be an offshore drilling system. The drilling rig 12 supports a drill string 16 that includes a bottomhole assembly 18 having a drill bit 20. The drilling rig 12 can rotate the drill string 16 (and its drill bit 20) to drill the well 14.

The drill string 16 is suspended within the well 14 from a hook 22 of the drilling rig 12 via a swivel 24 and a kelly 26. Although not depicted in FIG. 1, the skilled artisan will appreciate that the hook 22 can be connected to a hoisting system used to raise and lower the drill string 16 within the well 14. As one example, such a hoisting system could include a crown block and a drawworks that cooperate to raise and lower a traveling block (to which the hook 22 is connected) via a hoisting line. The kelly 26 is coupled to the drill string 16, and the swivel 24 allows the kelly 26 and the drill string 16 to rotate with respect to the hook 22. In the presently illustrated embodiment, a rotary table 28 on a drill floor 30 of the drilling rig 12 is constructed to grip and turn the kelly 26 to drive rotation of the drill string 16 to drill the well 14. In other embodiments, however, a top drive system could instead be used to drive rotation of the drill string 16.

During operation, drill cuttings or other debris may collect near the bottom of the well 14. Drilling fluid 32, also referred to as drilling mud, can be circulated through the well 14 to remove this debris. The drilling fluid 32 may also clean and cool the drill bit 20 and provide positive pressure within the well 14 to inhibit formation fluids from entering the wellbore. In FIG. 1, the drilling fluid 32 is circulated through the well 14 by a pump 34. The drilling fluid 32 is pumped from a mud pit (or some other reservoir, such as a mud tank) into the drill string 16 through a supply conduit 36, the swivel 24, and the kelly 26. The drilling fluid 32 exits near the bottom of the drill string 16 (e.g., at the drill bit 20) and returns to the surface through the annulus 38 between the wellbore and the drill string 16. A return conduit 40 transmits the returning drilling fluid 32 away from the well 14. In some embodiments, the returning drilling fluid 32 is cleansed (e.g., via one or more shale shakers, desanders, or desilters) and reused in the well 14.

In addition to the drill bit 20, the bottomhole assembly 18 also includes various instruments that measure information of interest within the well 14. For example, as depicted in FIG. 1, the bottomhole assembly 18 includes a logging-while-drilling (LWD) module 44 and a measurement-while-drilling (MWD) module 46. Both modules include sensors, housed in drill collars, that collect data and enable the creation of measurement logs in real-time during a drilling operation. The modules could also include memory devices for storing the measured data. The LWD module 44 includes sensors that measure various characteristics of the rock and formation fluid properties within the well 14. Data collected by the LWD module 44 could include measurements of gamma rays, resistivity, neutron porosity, formation density, sound waves, optical density, and the like. The MWD module 46 includes sensors that measure various characteristics of the bottomhole assembly 18 and the wellbore, such as orientation (azimuth and inclination) of the drill bit 20, torque, shock and vibration, the weight on the drill bit 20, and downhole temperature and pressure. The data collected by the MWD module 46 can be used to control drilling operations. The bottomhole assembly 18 can also include one or more additional modules 48, which could be LWD modules, MWD modules, or some other modules. It is noted that the bottomhole assembly 18 is modular, and that the positions and presence of particular modules of the assembly could be changed as desired. Further, as discussed in greater detail below, one or more of the modules 44, 46, and 48 is or includes a fluid sampling tool configured to obtain a sample of a fluid from a subterranean formation and perform downhole fluid analysis to measure optical densities of the sampled fluid, which can then be used to determine asphaltene content of the fluid.

The bottomhole assembly 18 can also include other modules. As depicted in FIG. 1 by way of example, such other modules include a power module 50, a steering module 52, and a communication module 54. In one embodiment, the power module 50 includes a generator (such as a turbine) driven by flow of drilling mud through the drill string 16. In other embodiments the power module 50 could also or instead include other forms of power storage or generation, such as batteries or fuel cells. The steering module 52 may include a rotary-steerable system that facilitates directional drilling of the well 14. The communication module 54 enables communication of data (e.g., data collected by the LWD module 44 and the MWD module 46) between the bottomhole assembly 18 and the surface. In one embodiment, the communication module 54 communicates via mud pulse telemetry, in which the communication module 54 uses the drilling fluid 32 in the drill string as a propagation medium for a pressure wave encoding the data to be transmitted.

The drilling system 10 also includes a monitoring and control system 56. The monitoring and control system 56 can include one or more computer systems that enable monitoring and control of various components of the drilling system 10. The monitoring and control system 56 can also receive data from the bottomhole assembly 18 (e.g., data from the LWD module 44, the MWD module 46, and the additional module 48) for processing and for communication to an operator, to name just two examples. While depicted on the drill floor 30 in FIG. 1, it is noted that the monitoring and control system 56 could be positioned elsewhere, and that the system 56 could be a distributed system with elements provided at different places near or remote from the well 14.

Figure 2:
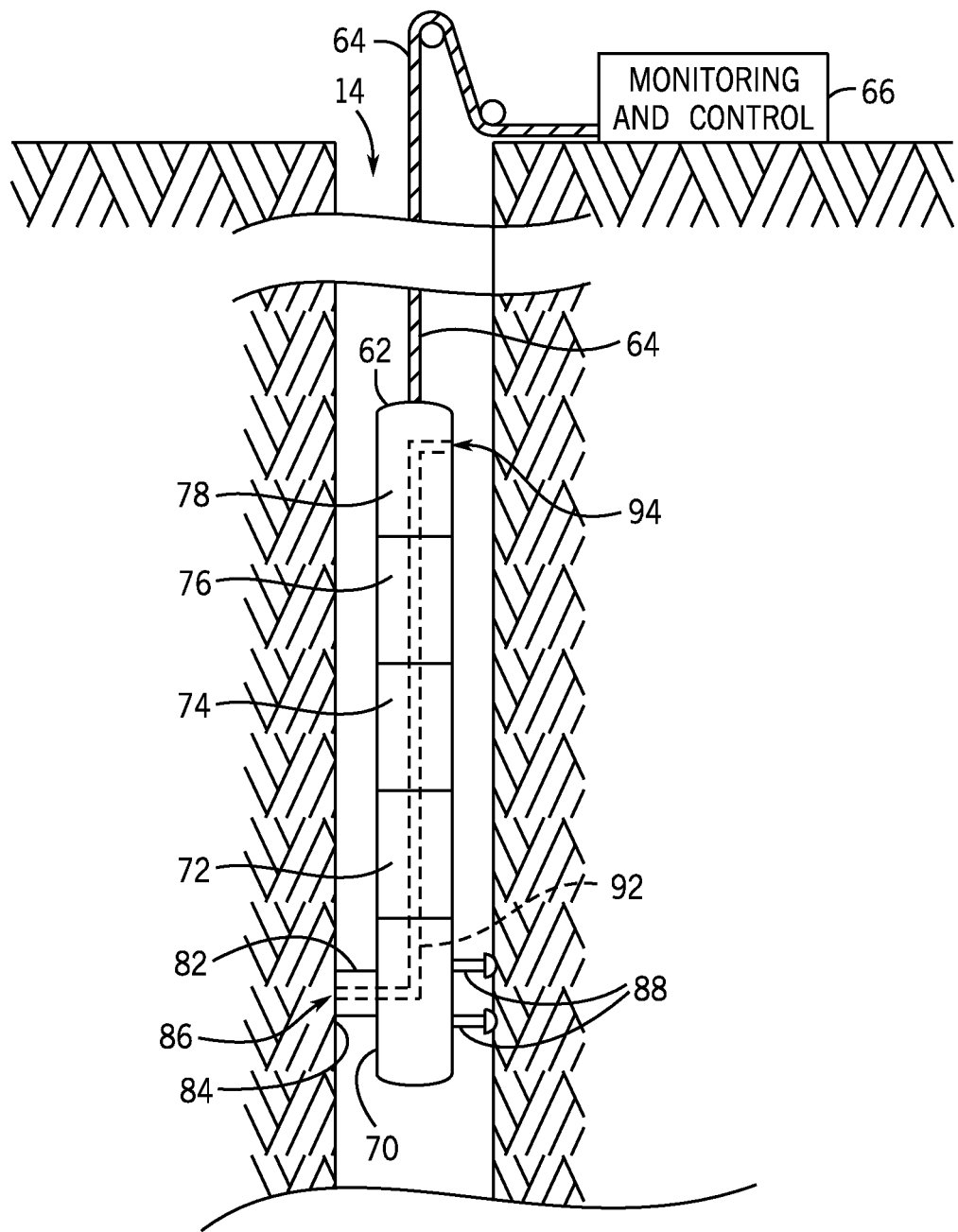
FIG. 2 generally depicts a fluid sampling tool deployed within a well on a wireline in accordance with one embodiment.

Another example of using a downhole tool for formation testing within the well 14 is depicted in FIG. 2. In this embodiment, a fluid sampling tool 62 is suspended in the well 14 on a cable 64. The cable 64 may be a wireline cable with at least one conductor that enables data transmission between the fluid sampling tool 62 and a monitoring and control system 66. The cable 64 may be raised and lowered within the well 14 in any suitable manner. For instance, the cable 64 can be reeled from a drum in a service truck, which may be a logging truck having the monitoring and control system 66. The monitoring and control system 66 controls movement of the fluid sampling tool 62 within the well 14 and receives data from the fluid sampling tool 62. In a similar fashion to the monitoring and control system 56 of FIG. 1, the monitoring and control system 66 may include one or more computer systems or devices and may be a distributed computing system. The received data can be stored, communicated to an operator, or processed, for instance. While the fluid sampling tool 62 is here depicted as being deployed by way of a wireline, in some embodiments the fluid sampling tool 62 (or at least its functionality) is incorporated into or as one or more modules of the bottomhole assembly 18, such as the LWD module 44 or the additional module 48.

The fluid sampling tool 62 can take various forms. While it is depicted in FIG. 2 as having a body including a probe module 70, a fluid analysis module 72, a pump module 74, a power module 76, and a fluid storage module 78, the fluid sampling tool 62 may include different modules in other embodiments. The probe module 70 includes a probe 82 that may be extended (e.g., hydraulically driven) and pressed into engagement against a wall 84 of the well 14 to draw fluid from a formation into the fluid sampling tool 62 through an intake 86. As depicted, the probe module 70 also includes one or more setting pistons 88 that may be extended outwardly to engage the wall 84 and push the end face of the probe 82 against another portion of the wall 84. In some embodiments, the probe 82 includes a sealing element or packer that isolates the intake 86 from the rest of the wellbore. In other embodiments the fluid sampling tool 62 could include one or more inflatable packers that can be extended from the body of the fluid sampling tool 62 to circumferentially engage the wall 84 and isolate a region of the well 14 near the intake 86 from the rest of the wellbore. In such embodiments, the extendable probe 82 and setting pistons 88 could be omitted and the intake 86 could be provided in the body of the fluid sampling tool 62, such as in the body of a packer module housing an extendable packer.

The pump module 74 draws the sampled formation fluid into the intake 86, through a flowline 92, and then either out into the wellbore through an outlet 94 or into a storage container (e.g., a bottle within fluid storage module 78) for transport back to the surface when the fluid sampling tool 62 is removed from the well 14. The fluid analysis module 72 includes one or more sensors for measuring properties of the sampled formation fluid, such as the optical density of the fluid, and the power module 76 provides power to electronic components of the fluid sampling tool 62.

The drilling and wireline environments depicted in FIGS. 1 and 2 are examples of environments in which a fluid sampling tool may be used to facilitate analysis of a downhole fluid. The presently disclosed techniques, however, could be implemented in other environments as well. For instance, the fluid sampling tool 62 may be deployed in other manners, such as by a slickline, coiled tubing, or a pipe string.

Figure 3:
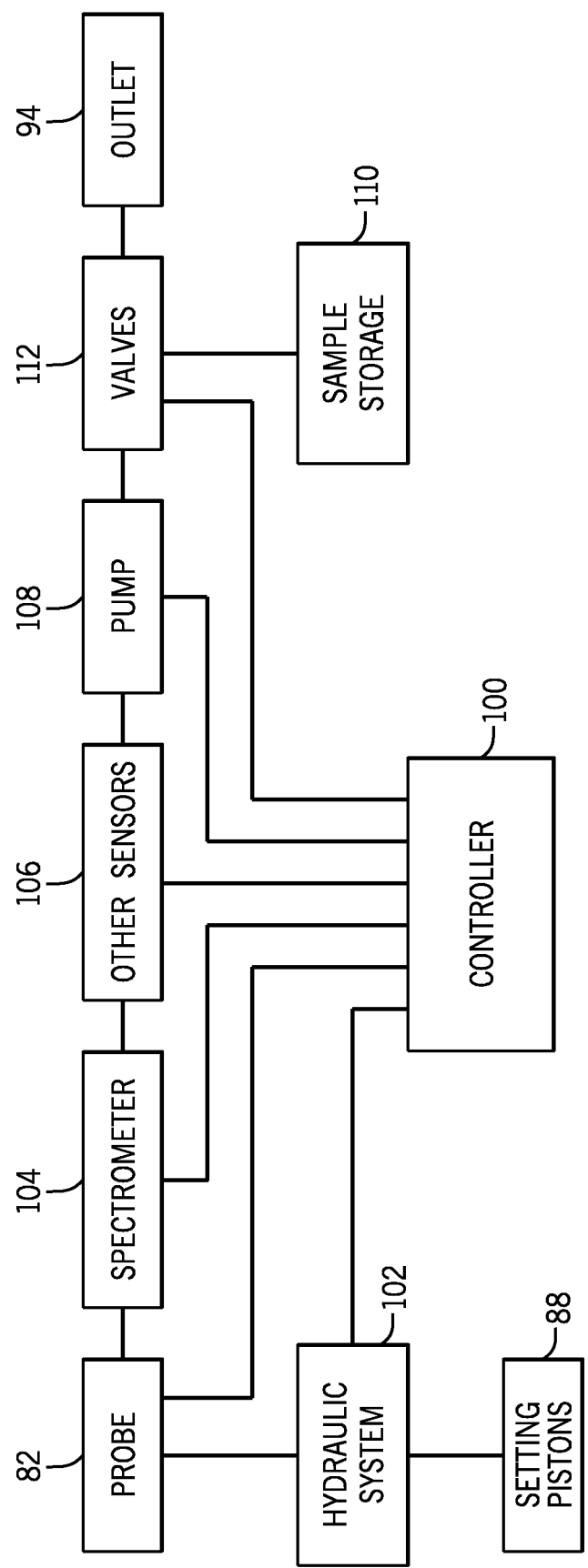
FIG. 3 is a block diagram of components of a fluid sampling tool operated by a controller in accordance with one embodiment.

Additional details as to the construction and operation of the fluid sampling tool 62 may be better understood through reference to FIG. 3. As shown in this figure, various components for carrying out functions of the fluid sampling tool 62 are connected to a controller 100. The various components include a hydraulic system 102 connected to the probe 82 and the setting pistons 88, a spectrometer 104 for measuring fluid optical properties, one or more other sensors 106, a pump 108, and valves 112 for diverting sampled fluid into storage devices 110 rather than venting it through the outlet 94.

In operation, the hydraulic system 102 extends the probe 82 and the setting pistons 88 to facilitate sampling of a formation fluid through the wall 84 of the well 14. It also retracts the probe 82 and the setting pistons 88 to facilitate subsequent movement of the fluid sampling tool 62 within the well. The spectrometer 104, which can be positioned within the fluid analysis module 72, collects data about optical properties of the sampled formation fluid. As discussed in greater detail below, such measured optical properties may include optical densities of the sampled formation fluid at different wavelengths of electromagnetic radiation. Other sensors 106 can be provided in the fluid sampling tool 62 (e.g., as part of the probe module 70 or the fluid analysis module 72) to take additional measurements related to the sampled fluid. In various embodiments, these additional measurements could include pressure and temperature, density, viscosity, electrical resistivity, saturation pressure, and fluorescence, to name several examples. Any suitable pump 108 may be provided in the pump module 74 to enable formation fluid to be drawn into and pumped through the flowline 92 in the manner discussed above. Storage devices 110 for formation fluid samples can include any suitable vessels (e.g., bottles) for retaining and transporting desired samples within the fluid sampling tool 62 to the surface. Both the storage devices 110 and the valves 112 may be provided as part of the fluid storage module 78.

In the embodiment depicted in FIG. 3, the controller 100 facilitates operation of the fluid sampling tool 62 by controlling various components. Specifically, the controller 100 directs operation (e.g., by sending command signals) of the hydraulic system 102 to extend and retract the probe 82 and the setting pistons 88 and of the pump 108 to draw formation fluid samples into and through the fluid sampling tool. The controller 100 also receives data from the spectrometer 104 and the other sensors 106. This data can be stored by the controller 100 or communicated to another system (e.g., the monitoring and control system 56 or 66) for analysis. In some embodiments, the controller 100 is itself capable of analyzing the data it receives from the spectrometer 104 and the other sensors 106. The controller 100 also operates the valves 112 to divert sampled fluids from the flowline 92 into the storage devices 110.

Figure 4:
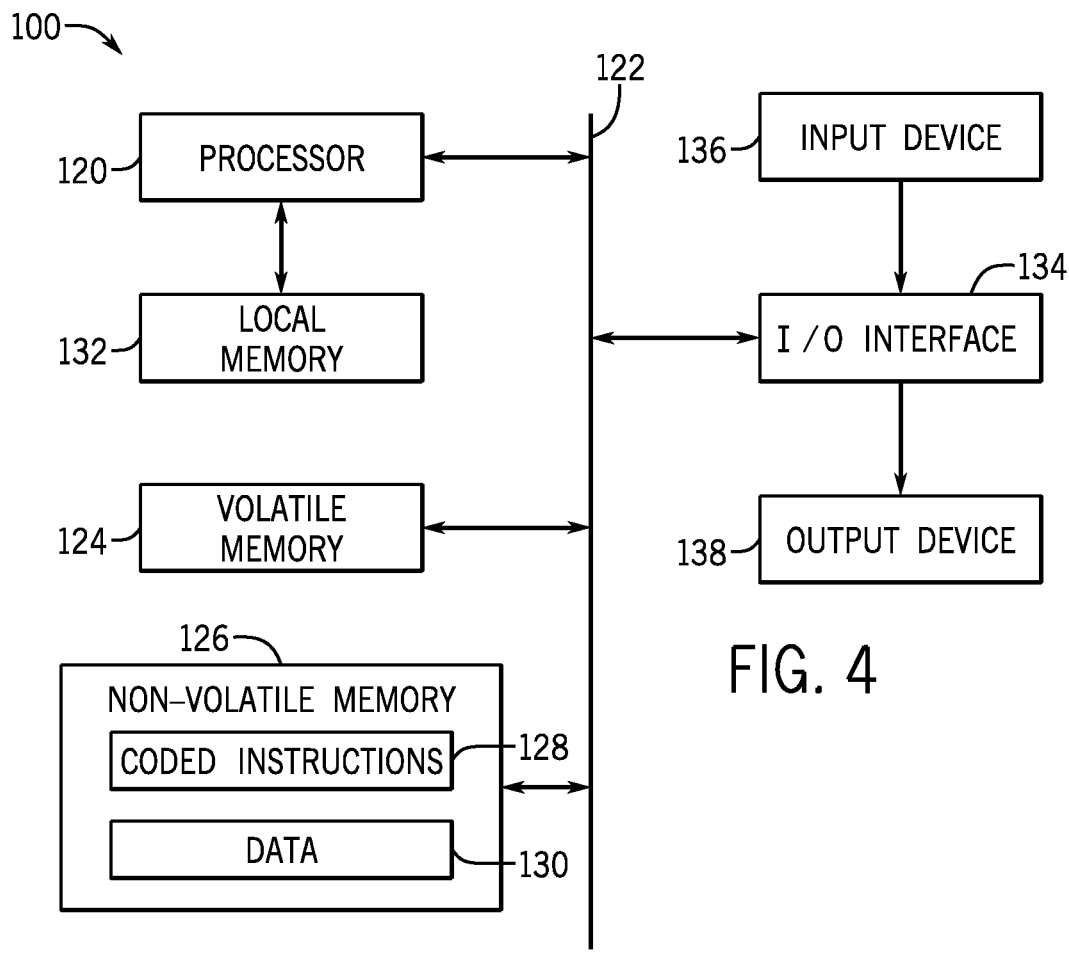
FIG. 4 is a block diagram of components in one example of the controller illustrated in FIG. 3.

The controller 100 in some embodiments is a processor-based system, an example of which is provided in FIG. 4. In this depicted embodiment, the controller 100 includes at least one processor 120 connected, by a bus 122, to volatile memory 124 (e.g., random-access memory) and non-volatile memory 126 (e.g., flash memory and a read-only memory (ROM)). Coded application instructions 128 (e.g., software that may be executed by the processor 120 to enable the control and analysis functionality described herein) and data 130 are stored in the non-volatile memory 126. For example, the application instructions 128 can be stored in a ROM and the data can be stored in a flash memory. The instructions 128 and the data 130 may be also be loaded into the volatile memory 124 (or in a local memory 132 of the processor) as desired, such as to reduce latency and increase operating efficiency of the controller 100.

An interface 134 of the controller 100 enables communication between the processor 120 and various input devices 136 and output devices 138. The interface 134 can include any suitable device that enables such communication, such as a modem or a serial port. In some embodiments, the input devices 136 include one or more sensing components of the fluid sampling tool 62 (e.g., the spectrometer 104) and the output devices 138 include displays, printers, and storage devices that allow output of data received or generated by the controller 100. Input devices 136 and output devices 138 may be provided as part of the controller 100, although in other embodiments such devices may be separately provided.

The controller 100 can be provided as part of the monitoring and control systems 56 or 66 outside of a well 14 to enable downhole fluid analysis of samples obtained by the fluid sampling tool 62. In such embodiments, data collected by the fluid sampling tool 62 can be transmitted from the well 14 to the surface for analysis by the controller 100. In some other embodiments, the controller 100 is instead provided within a downhole tool in the well 14, such as within the fluid sampling tool 62 or in another component of the bottomhole assembly 18, to enable downhole fluid analysis to be performed within the well 14. Further, the controller 100 may be a distributed system with some components located in a downhole tool and others provided elsewhere (e.g., at the surface of the wellsite).

Whether provided within or outside the well 14, the controller 100 can receive data collected by the sensors within the fluid sampling tool 62 and process this data to determine one or more characteristics of the sampled fluid. Examples of such characteristics include fluid type, gas-to-oil ratio, carbon dioxide content, water content, contamination, and, as discussed in greater detail below, asphaltene content.

Some of the data collected by the fluid sampling tool 62 relates to optical properties (e.g., optical densities) of a sampled fluid measured by the spectrometer 104. To facilitate measurements, in some embodiments the spectrometer 104 may be arranged about the flowline 92 of the fluid sampling tool 62 in the manner generally depicted in FIG. 5. In this example, the spectrometer 104 includes an emitter 142 of electromagnetic radiation, such as a light source, and a detector 144 disposed about the flowline 92 in the fluid sampling tool 62. A light source provided as the emitter 142 can be any suitable light-emitting device, such as one or more light-emitting diodes or incandescent lamps. As used herein, the term "visible light" is intended to mean electromagnetic radiation within the visible spectrum, and the shorter term "light" is intended to include not just electromagnetic radiation within the visible spectrum, but also infrared and ultraviolet radiation.

Figure 5:
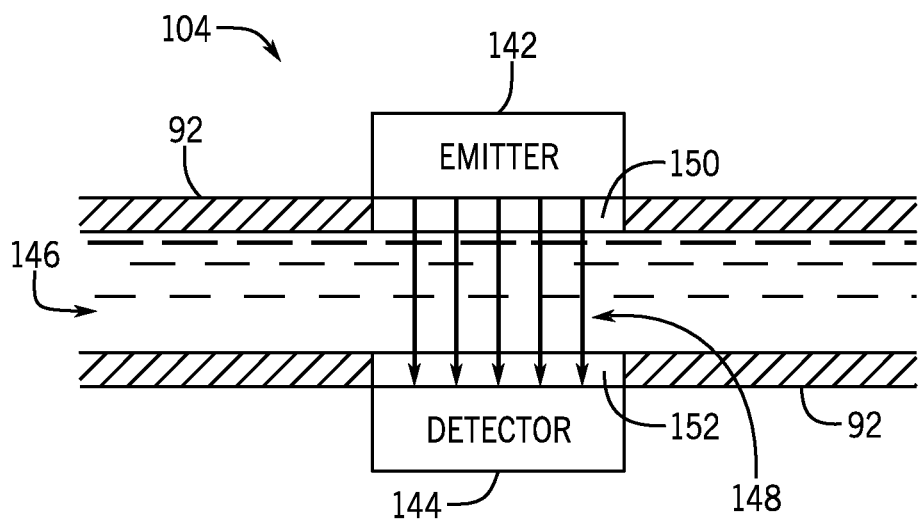
FIG. 5 generally depicts a spectrometer positioned about a flowline to enable measurement of an optical property of a fluid within the flowline in accordance with one embodiment.

In operation, a sampled formation fluid 146 within the flowline 92 is irradiated with electromagnetic radiation 148 (e.g., light) from the emitter 142. The electromagnetic radiation 148 includes radiation of any desired wavelengths within the electromagnetic spectrum. In some embodiments, the electromagnetic radiation 148 has a continuous spectrum within one or both of the visible range and the short- and near-infrared (SNIR) range of the electromagnetic spectrum, and the detector 144 filters or diffracts the received electromagnetic radiation 148. The detector 144 may include a plurality of detectors each assigned to separately measure light of a different wavelength. As depicted in FIG. 5, the flowline 92 includes windows 150 and 152 that isolate the emitter 142 and the detector 144 from the sampled formation fluid 146 while still permitting the electromagnetic radiation 148 to be transmitted and measured. As will be appreciated, some portion of the electromagnetic radiation 148 is absorbed by the sampled fluid 146, and the extent of such absorption varies for different wavelengths and sampled fluids. The optical density of the fluid 146 at one or more wavelengths may be determined based on data from the spectrometer 104 by comparing the amount of radiation emitted by the emitter 142 and the amount of that radiation received at detector 144. It will be appreciated that the optical density (also referred to as the absorbance) of a fluid at a given wavelength is calculated as the base-ten logarithm of the ratio of electromagnetic radiation incident on the fluid to that transmitted through the fluid for the given wavelength.

The spectrometer 104 may include any suitable number of measurement channels for detecting different wavelengths, and may include a filter-array spectrometer or a grating spectrometer. For example, in some embodiments the spectrometer 104 is a filter-array absorption spectrometer having sixteen measurement channels. In other embodiments, the spectrometer 104 may have ten channels or twenty channels, and may be provided as a filter-array spectrometer or a grating spectrometer. Further, as noted above and described in greater detail below, the data obtained with the spectrometer 104 can be used to determine optical densities and asphaltene content of sampled fluids.

Figure 6:
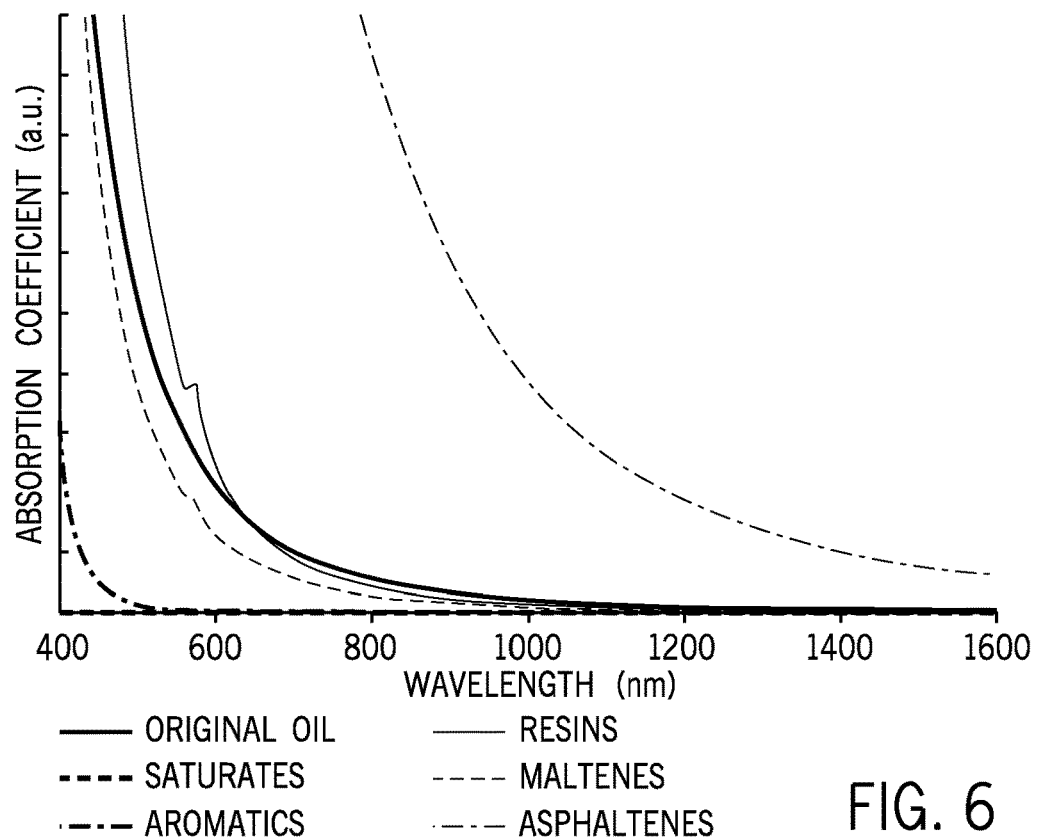
FIG. 6 is a graph representing optical spectra of a stock tank oil and its components for wavelengths in the visible and short- and near-infrared ranges in accordance with one embodiment.

By way of example, FIG. 6 illustrates examples of absorbance spectra for a stock tank oil (STO) and for various components extracted from the stock tank oil. Particularly, this figure depicts the absorbance spectra for the stock tank oil (denoted "original oil" in this figure), as well as for components (i.e., asphaltenes, maltenes, saturates, aromatics, and resins) extracted from the stock tank oil. It is noted that maltenes are the non-asphaltene portion of a petroleum mixture and that these maltenes include saturates, aromatics, and resins. The absorbance spectra of FIG. 6 are depicted as a function of wavelength of electromagnetic radiation, which ranges in the present figure from 400 nm to 1600 nm (within the visible wavelength range and the SNIR wavelength range). The stock tank oil spectrum can be described as a linear combination of the asphaltene, resin, aromatic, and saturate spectra as follows:

$$\Omega_{STO}(\lambda) = \Omega_{Asp}(\lambda) + \Omega_{Res}(\lambda) + \Omega_{Aro}(\lambda) + \Omega_{Sat}(\lambda) \quad (1)$$

$$= \varepsilon_{Asp}(\lambda) \cdot c_{Asp} \cdot l + \varepsilon_{Res}(\lambda) \cdot c_{Res} \cdot l + \varepsilon_{Aro}(\lambda) \cdot c_{Aro} \cdot l +$$

$$\varepsilon_{Sat}(\lambda) \cdot c_{Sat} \cdot l$$

where $\Omega_i(\lambda)$ is the optical density at wavelength $\lambda$ for items i (that is, stock tank oil (STO), asphaltene (Asp), resin (Res), aromatic (Aro), and saturate (Sat)); $\varepsilon_i$ is the absorption coefficient of a component i of the stock tank oil at wavelength $\lambda$; $c_i$ is the mass concentration of component i; and l is the optical path length (that is, the distance traveled across the fluid by electromagnetic radiation received by a detector, such as the inner diameter of the flowline 92).

With reference to FIG. 6, it is noted that the absorption coefficients of aromatic and saturate components are generally negligible compared to those of asphaltene and resin components in much of the visible-SNIR wavelength range (e.g., 600-1600 nm in this figure). Consequently, the optical density of stock tank oil can be approximated as the sum of the optical densities of asphaltene and resin in this wavelength region:

$$\Omega_{STO}(\lambda) \approx \Omega_{Asp}(\lambda) + \Omega_{Res}(\lambda) = \varepsilon_{Asp}(\lambda) \cdot c_{Asp} \cdot l + \varepsilon_{Res}(\lambda) \cdot c_{Res} \cdot l \quad (2)$$

From Equation 2 above, the optical density of a stock tank oil can be written by using the absorption coefficients at a specified wavelength $\lambda$, the masses of asphaltene ($m_{Asp}$) and resin ($m_{Res}$) in the stock tank oil volume (V), and the optical path length (l) as follows:

$$\Omega_{STO}(\lambda) \approx \varepsilon_{Asp}(\lambda) \cdot \frac{m_{Asp}}{V} \cdot l + \varepsilon_{Res}(\lambda) \cdot \frac{m_{Res}}{V} \cdot l \quad (3)$$

$$\text{where } c_i = \frac{m_i}{V} \quad (4)$$

Also, dividing both sides of Equation 3 with the density of the stock tank oil ($\rho_{STO}$) allows the equation to be rewritten as:

$$\frac{\Omega_{STO}(\lambda)}{\rho_{STO}} = \varepsilon_{Asp}(\lambda) \cdot \frac{m_{Asp}}{M_{STO}} \cdot l + \varepsilon_{Res}(\lambda) \cdot \frac{m_{Res}}{M_{STO}} \cdot l \quad (5)$$

$$\text{where } \rho_{STO} = \frac{M_{STO}}{V} \quad (6)$$

Thus, the asphaltene content in mass fraction is related to the optical density of stock tank oil from Equation 5:

$$\frac{m_{Asp}}{M_{STO}} = \frac{1}{\varepsilon_{Asp}(\lambda) \cdot \rho_{STO} \cdot l} \cdot \Omega_{STO} - \frac{\varepsilon_{Res}(\lambda)}{\varepsilon_{Asp}(\lambda)} \cdot \frac{m_{Res}}{M_{STO}} \quad (7)$$
$$= a \cdot \Omega_{STO} + b$$

$$\text{where } a = \frac{1}{\varepsilon_{Asp}(\lambda) \cdot \rho_{STO} \cdot l}, \; b = -\frac{\varepsilon_{Res}(\lambda)}{\varepsilon_{Asp}(\lambda)} \cdot \frac{m_{Res}}{M_{STO}} \quad (8)$$

As may be seen from Equations 7 and 8, the coefficients a and b depend on $\varepsilon_i$, $\rho_{STO}$, and resin content ($m_{Res}/M_{STO}$), which are undetermined parameters. Also, in order to obtain optical density of a stock tank oil ($\Omega_{STO}$), live crude oil could be flashed at a standard, surface condition (e.g., 60° F., 14.7 psia) to remove gaseous components and then allow the measurement of the optical density of the remaining liquid portion of the sample. In downhole environments, however, flashing a fluid sample while it is downhole to determine $\Omega_{STO}$ is generally infeasible.

In accordance with certain embodiments, a relationship between asphaltene content and optical density of live crude oil can instead be derived using formation volume factor ($B_o$) via Equation 7 above. The formation volume factor of a live crude oil can be estimated using downhole optical spectrometer data as follows:

$$B_o = \frac{\Omega_{STO}(\lambda)}{\Omega_{L.O.}(\lambda)} \cdot \left(1 + \sum_i \tilde{\varepsilon}_i(\lambda) \cdot \mu_i \cdot \frac{\tilde{\rho}_i}{\sum_k (1-\mu_k)\tilde{\rho}_k}\right), \quad (9)$$

$$\text{for } (i, k : C1, C2, C3, C4, C5, C6+ \text{ and } CO2)$$

where $\Omega_{L.O.}$ is the optical density of a live crude oil at wavelength $\lambda$, $\Omega_{STO}$ is the optical density of stock tank oil averaged over database samples at wavelength $\lambda$, $\tilde{\rho}_i/\rho_i/\rho_{C6+}$ and is the relative concentration of a hydrocarbon component, $\tilde{\varepsilon}_i(\lambda)/\varepsilon_i(\lambda)/\varepsilon_{C6+}(\lambda)$ and is the relative absorption coefficient of a hydrocarbon component, and $\mu_k$ is the vapor fraction of a hydrocarbon component. In at least some embodiments, the formation volume factor can be determined in a hydrocarbon absorption region (e.g., $\lambda$ between 1600 nm and 1800 nm) using Equation 9.

The optical density of a live crude oil ($\Omega_{L.O.}$) can be measured downhole (e.g., via spectrometer 104) and the optical density of stock tank oil can be predetermined by averaging stock tank oil optical densities of database samples. Relative concentrations and vapor fractions of the hydrocarbon components can be obtained in any suitable manner, such as from a near-infrared optical spectrum of the sample, and relative absorption coefficients may be predetermined in any suitable fashion.

In the visible-SNIR wavelength region of electromagnetic radiation, the absorption coefficients of C1, C2, C3, C4, C5, and CO2 are approximately zero. The absorption coefficient of C6+ components, which have vapor fractions in the standard condition, is also assumed to be zero (in fact, vapor is colorless). Consequently, the formation volume factor can be estimated using optical density in the visible-SNIR wavelength range as follows:

$$B_o = \frac{\Omega_{STO}(\lambda)}{\Omega_{L.O.}(\lambda)} \quad (10)$$

$$\lambda: \text{visible-}SNIR$$

In other words:

$$\Omega_{STO}(\lambda) = B_o \Omega_{L.O.}(\lambda) \quad (11)$$

Therefore, the asphaltene content in Equation 7 above can be related to the optical density of live crude oil as follows:

$$\frac{m_{Asp}}{M_{STO}} = a \cdot \Omega_{STO}(\lambda) + b = a \cdot B_0 \cdot \Omega_{L.O.}(\lambda) + b \quad (12)$$

The coefficients a and b can be determined to obtain asphaltene content from Equation 12. These coefficients can be calibrated and determined using a database containing optical spectra, formation volume factors, and asphaltene contents of crude oils. However, according to Equation 8, the coefficients a and b depend on the following parameters: stock tank oil density ($\rho_{STO}$); absorption coefficients of asphaltene ($\varepsilon_{Asp}$) and resin ($\varepsilon_{Res}$), since they are sample dependent; and the resin content ($m_{Res}/M_{STO}$). As such, the calibrated coefficients a and b have a range of variations associated with variation of these parameters in Equation 8.

Figure 7:
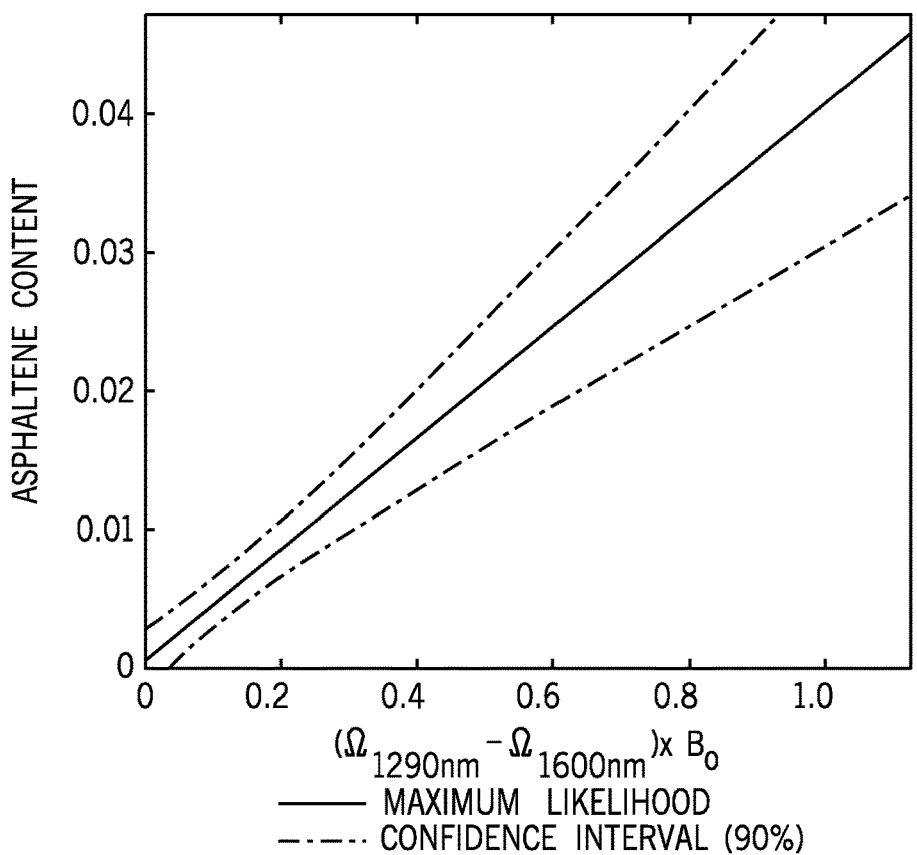
FIG. 7 is a graph depicting a calibration curve relating asphaltene content to optical densities of live crude oils and their formation volume factors in accordance with one embodiment.

An example of a calibration curve of asphaltene content against optical density of stock tank oils estimated from optical densities of live crude oils and their formation volume factors in a database is depicted in FIG. 7. In one embodiment, the database used for the calibration includes over one hundred crude oil spectra in a temperature range from 75° C. to 175° C. and in a pressure range from 5,000 psi to 20,000 psi. Other embodiments, however, may rely on a different number of spectra across different temperature and pressure ranges.

In FIG. 7, the vertical axis indicates asphaltene content (expressed as a weight ratio) obtained from known techniques, such as in accordance with ASTM D2007-80 or ASTM D6560 standards promulgated by ASTM International, which are conventionally used in a Pressure-Volume-Temperature (PVT) laboratory. These standards may also be referred to as a modified IP 143 method. The horizontal axis is related to the estimated optical density of stock tank oils from Equation 11 above. While some embodiments may simply use the estimated optical density alone, in other embodiments a difference between the optical densities of two channels is used to avoid spectral offset due to light scattering by particles and refractive indices of samples. In the present example of FIG. 7, optical densities at 1290 nm and 1600 nm (i.e., $\Omega(1290\ nm)$ and $\Omega(1600\ nm)$) were used and scaled by the estimated formation volume factor for the calibration: $(\Omega(1290\ nm)-\Omega(1600\ nm))\times B_o$. The calibration curve can be obtained in any suitable manner, such as by using a bootstrap resampling method or other resampling technique. The solid line in FIG. 7 indicates the maximum likelihood of estimates, where a equals the slope of the solid line and b equals its y-intercept. The dashed lines indicate a 90% confidence interval associated with the range of variation of a and b, although other confidence levels could be used (e.g., a 95% confidence interval).

Figure 8:
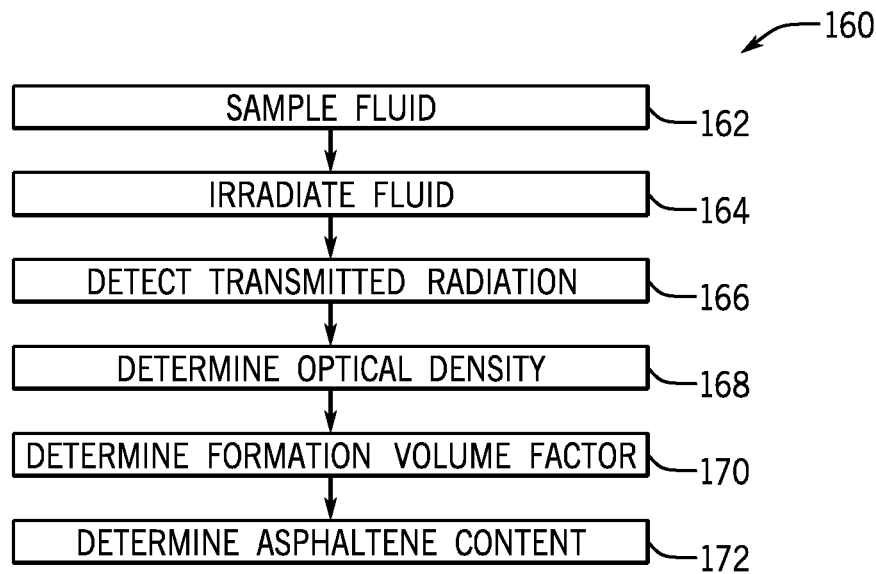
FIG. 8 is a flow chart for determining asphaltene content of a fluid using its optical density and formation volume factor in accordance with one embodiment.

One example of a process for estimating asphaltene content of a fluid (e.g., crude oil) is generally represented by flow chart 160 in FIG. 8. In this embodiment, a sample of a formation fluid is obtained (block 162). For instance, a live crude oil may be sampled by a downhole tool (e.g., routed into the downhole fluid sampling tool 62). The fluid sample is then irradiated (block 164) with electromagnetic radiation and some amount of this radiation that is transmitted through the fluid is detected (block 166). This irradiation and detection can be performed by any of various suitable spectrometers, such as spectrometer 104 described above. Further, in at least some embodiments the detected electromagnetic radiation includes radiation within the visible-SNIR wavelength range. One or more optical densities may then be determined (block 168) for the sampled formation fluid based on the spectroscopic data. Further, a formation volume factor for the sampled fluid can be determined (block 170), such as by calculating the formation volume factors as described above. The asphaltene content of the sampled formation fluid can then be determined (block 172) from the optical density and formation volume factor for the fluid.

Figure 9:
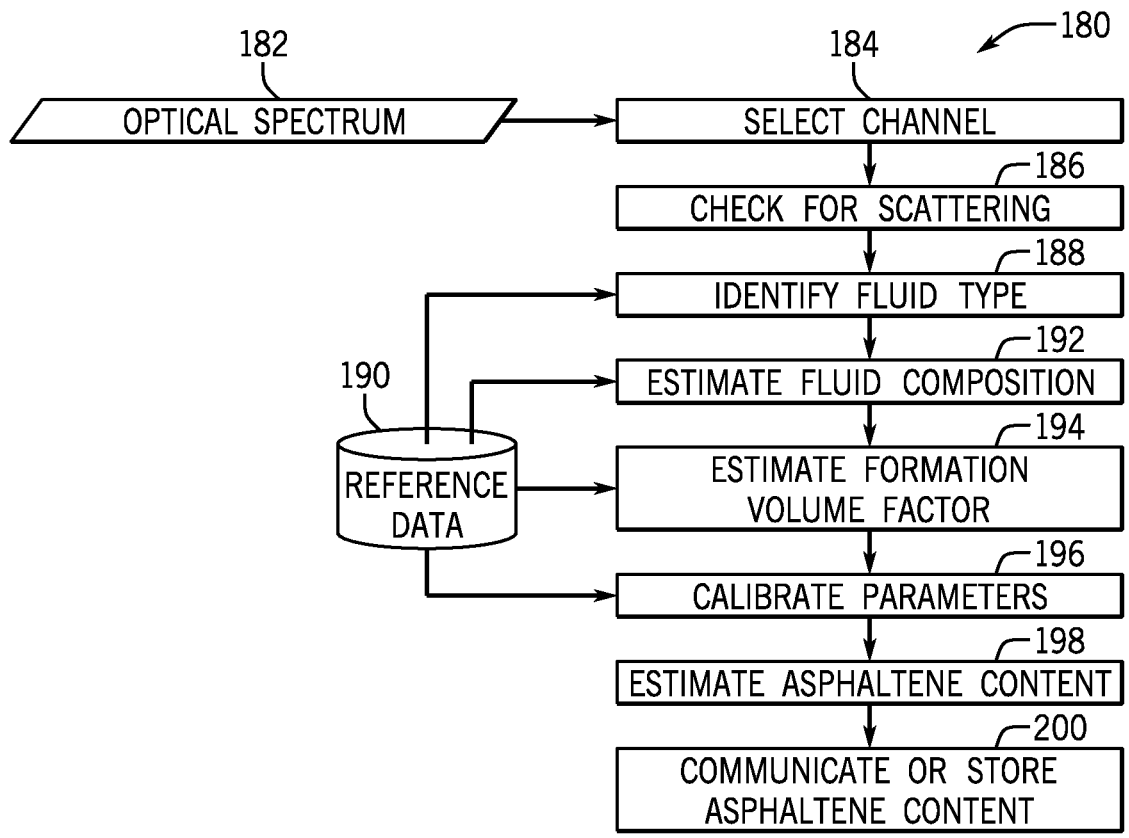
FIG. 9 is a flow chart for determining asphaltene content of a fluid in accordance with another embodiment.

Another example of a process for determining asphaltene content of a fluid (e.g., crude oil) is generally represented by flow chart 180 in FIG. 9. The depicted process has an input of an optical spectrum 182 for a crude oil as measured by a spectrometer. For instance, in one embodiment the optical spectrum 182 is obtained for a live crude oil using the spectrometer 104 downhole during a sampling operation for wireline or while drilling. The optical spectrum 182 may be represented by data obtained over multiple measurement channels (which may also be referred to as wavelength channels) of a spectrometer. Generally, this data can be collected by routing a fluid sample into a tool (such as a downhole tool within a well) and using a spectrometer of the tool to irradiate the sampled fluid and detect radiation transmitted through the fluid. Optical densities for the sampled fluid can also be calculated as described above.

As depicted in the flow chart 180, a wavelength channel of the spectrometer may be selected (block 184). In one embodiment, the selected wavelength channel is between 800 nm and 1500 nm. The wavelength channel can be selected based on any desired criteria. For instance, as measurements may be less reliable if the optical density is too high, selection of the wavelength channel can include comparing the measured optical densities for one or more wavelength channels to an optical density threshold (e.g., an optical density threshold of three). In such an embodiment, selecting the wavelength channel may include disregarding wavelength channels that are determined to have measured optical densities above the threshold before finding a suitable wavelength channel with a measured optical density below the threshold.

Once an appropriate wavelength channel is found, presence of light scattering of electromagnetic radiation measured by the selected wavelength can be assessed (block 186) in any suitable manner. Light scattering, particularly wavelength-dependent scattering, may cause over-fluctuation of optical density. If the scattering is more than negligible (e.g., above a scattering threshold), another wavelength channel can be selected as described above. If the scattering is negligible (e.g., below a scattering threshold), a fluid type of the sampled fluid can then be identified (block 188) from data obtained by the spectrometer for the sampled fluid, such as the measured optical spectrum 182. For example, optical densities for one or more wavelength channels represented in the optical spectrum 182 can be compared to reference data in a database 190 that includes correlations between optical densities of previously analyzed fluids (e.g., through laboratory analysis) and their known fluid types to determine that the sampled fluid is oil or some other type of fluid. The database 190 can be stored in any suitable, non-transitory computer-readable storage medium, such as non-volatile memory 126.

If the fluid is identified as oil, the composition of the oil (block 192) and the formation volume factor (block 194) can be estimated as described above. Various data helpful in estimating the composition and formation volume factor, such as relative absorption coefficients of hydrocarbon components and optical densities of previously analyzed stock tank oil samples, can also be provided in the database 190. Parameters relating asphaltene content to optical density can be calibrated (block 196) by way of a calibration curve derived from resampling of data (which could be provided in the database 190) from previously measured crude oil optical spectra, as discussed above. The calibration of the parameters (which includes determining the parameters) in block 196 can be performed at any suitable time, including before obtaining the optical spectrum 182 or even before beginning a fluid sampling process. It is noted that the data used in the presently disclosed processes (e.g., such as reference data in database 190) may be provided in any suitable form, such as data representing one or more look-up tables, charts, graphs, or the like, and stored in any suitable memory.

In some embodiments, the product of the estimated formation volume factor and the optical density of the selected wavelength channel can be computed and then used to estimate (block 198) the asphaltene content of the sampled oil. In other embodiments, the estimated formation volume factor and optical densities of multiple wavelength channels could instead be used to estimate the asphaltene content. For instance, the product of the formation volume factor and the difference between the optical densities at a selected wavelength channel (e.g., at 1290 nm) and at a baseline channel (e.g., at 1600 nm) could be calculated and then used to estimate the asphaltene content of the sampled fluid. In at least some embodiments, estimating the asphaltene content includes using the product of the optical density at the selected wavelength channel (or the difference between optical densities at the selected wavelength channel and at a baseline channel) and the determined formation volume factor to obtain the maximum likelihood estimate of asphaltene content and its confidence interval from the calibration curve. The estimated asphaltene content can be communicated or stored for later use (block 200).

The processes generally represented by flow charts 160 and 180 can be carried out by any suitable devices or systems, such as the controller 100 (in which case the reference data 190 may be stored in a memory device within controller 100) in connection with a downhole tool (e.g., LWD module 44 or additional module 48 of FIG. 1, or fluid sampling tool 62 of FIG. 2). These suitable devices and systems can use algorithms, executable code, lookup tables, and the like to carry out the functionality described above. Also, in some embodiments these processes may be performed in substantially real time without removing fluid samples from the well 14.

Figure 10:
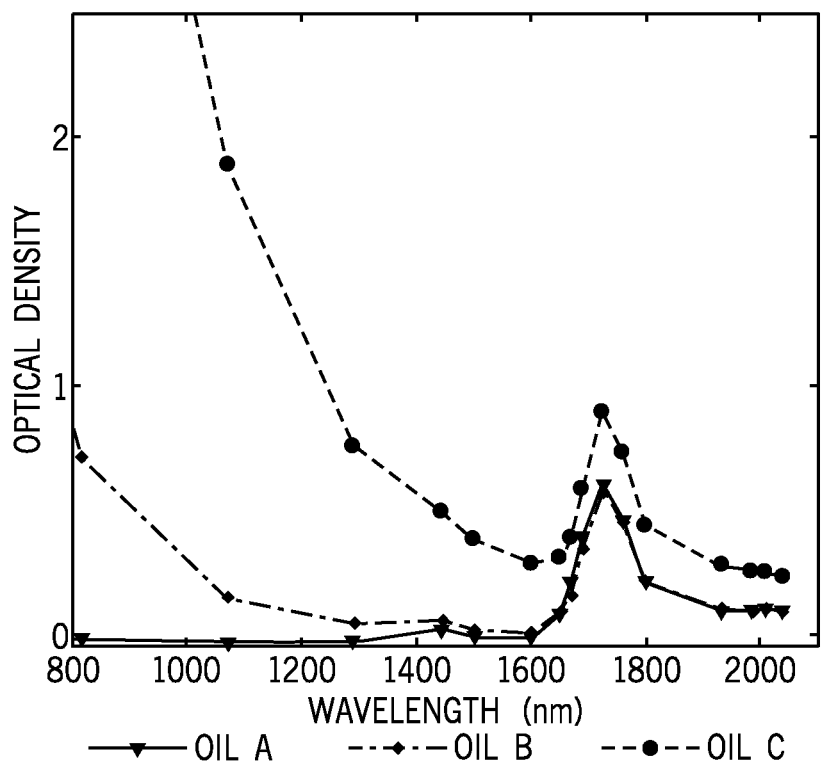
FIG. 10 graphically depicts optical spectra of test samples measured with a downhole optical spectrometer in accordance with one embodiment.

By way of further example, FIG. 10 depicts optical spectra of several test crude oil samples measured with a downhole optical spectrometer, such as spectrometer 104 described above. Properties of these test crude samples, including gas-to-oil ratio (GOR), American Petroleum Institute (API) gravity, temperature, and pressure for each sample, are provided in the following table:

TABLE 1

| Sample | GOR (scf/bbl) | API Gravity | Temperature (° C.) | Pressure (psia) |
| --- | --- | --- | --- | --- |
| Oil A | 810 | 36 | 175 | 10,000 |
| Oil B | 208 | 31 | 175 | 5,000 |
| Oil C | 184 | 17 | 125 | 15,000 |

Figure 11:
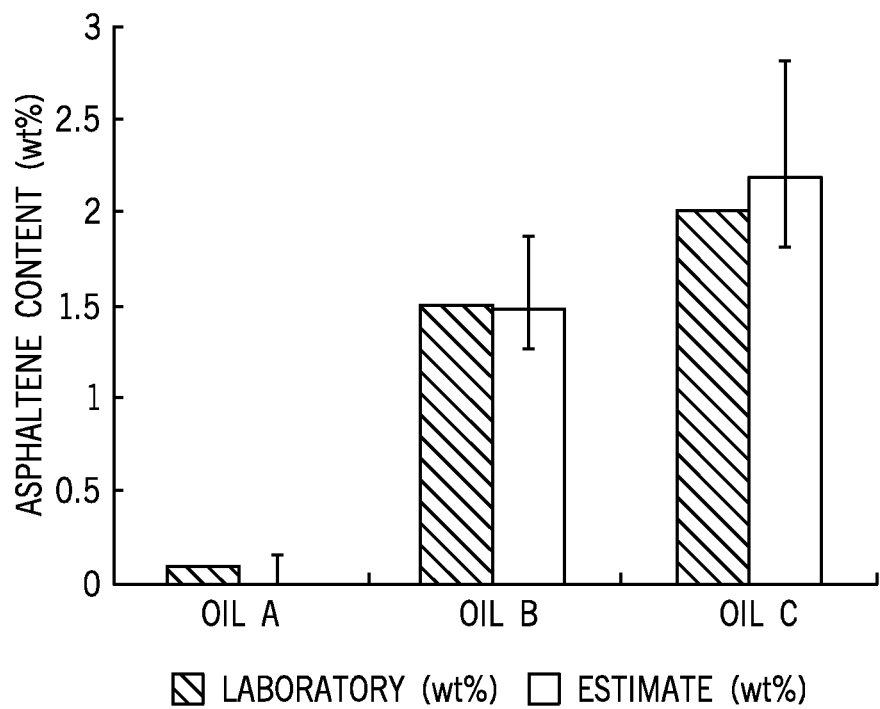
FIG. 11 is a graph comparing asphaltene contents estimated for the test samples of FIG. 10 through a standard laboratory procedure to asphaltene contents estimated using

Optical densities between 1500 nm and 2040 nm were used in this example for estimating fluid composition (e.g., C1, C2, C3, C4, C5, C6+, and CO2) and the formation volume factor. Then, the product $(\Omega(1290\ nm) - \Omega(1600\ nm)) \times B_o$ was calculated for the samples and used to estimate asphaltene content and 90% confidence intervals from the calibration curve of FIG. 7. A comparison of the estimated results with 90% confidence intervals (shown as vertical error bars) to results obtained from a laboratory analysis (i.e., with the modified IP 143 method) is graphically depicted in FIG. 11. As will be appreciated from this graph, the estimated asphaltene contents closely approximate the results obtained from the standard laboratory procedure.

The foregoing outlines features of several embodiments so that those skilled in the art may better understand aspects of the present disclosure. Those skilled in the art should appreciate that they may readily use the present disclosure as a basis for designing or modifying other processes and structures for carrying out the same purposes or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The invention claimed is:

1. A method comprising:
   measuring an optical density of a live crude oil within a well;
   calculating a formation volume factor of the live crude oil within the well based on the measured optical density, wherein the formation volume factor relates the measured optical density of the live crude oil within the well to an optical density of a stock tank oil; and
   determining asphaltene content of the live crude oil within the well based on the measured optical density and the calculated formation volume factor of the live crude oil within the well, and additional parameters that are derived from an analysis of optical spectra, formation volume factors, and asphaltene contents of previously sampled crude oils in a database.

2. The method of claim 1, wherein measuring the optical density of the live crude oil within the well includes measuring optical densities of the live crude oil within the well to electromagnetic radiation of a first wavelength and to electromagnetic radiation of a second wavelength.

3. The method of claim 2, wherein the electromagnetic radiation of the first wavelength and the electromagnetic radiation of the second wavelength are both infrared radiation.

4. The method of claim 3, wherein the first wavelength is 1290 nm and the second wavelength is 1600 nm.

5. The method of claim 1, wherein calculating the formation volume factor of the live crude oil within the well is also based on the optical density of the stock tank oil.

6. The method of claim 1, comprising determining the composition of the live crude oil within the well and using the determined composition in calculating the formation volume factor of the live crude oil within the well.

7. The method of claim 1, comprising performing the analysis of the optical spectra, formation volume factors, and asphaltene contents of the previously sampled crude oils.

8. The method of claim 7, wherein performing the analysis of the optical spectra, formation volume factors, and asphaltene contents of the previously sampled crude oils includes determining a calibration curve through resampling of data on the optical spectra, formation volume factors, and asphaltene contents collected for the previously sampled crude oils.

9. The method of claim 1, wherein the formation volume factor represents a ratio of the optical density of the stock tank oil to the measured optical density of the live crude oil of the well.

10. A method comprising:
    routing a fluid of a well into a downhole tool within the well, the downhole tool including a spectrometer having an emitter and a detector;
    irradiating the fluid of the well in the downhole tool with electromagnetic radiation from the emitter of the spectrometer;
    detecting a portion of the electromagnetic radiation that is transmitted through the fluid of the well with the detector of the spectrometer;
    determining an optical density of the fluid of the well based on the detected portion of the electromagnetic radiation transmitted through the fluid of the well;

calculating a formation volume factor of the fluid of the well based on the determined optical density, wherein the formation volume factor relates the determined optical density of the fluid of the well in the downhole tool to an optical density of a stock tank oil; and determining asphaltene content of the fluid of the well based on the determined optical density and the formation volume factor.

11. The method of claim 10, comprising selecting a measurement channel of the detector based on the optical density of the fluid of the well within the downhole tool as measured by the measurement channel.

12. The method of claim 11, wherein selecting the measurement channel includes determining that the optical density of the fluid of the well within the downhole tool as measured by the measurement channel is below an optical density threshold.

13. The method of claim 12, wherein selecting the measurement channel includes first determining that one or more additional optical densities of the fluid of the well within the downhole tool as measured by one or more other measurement channels are above the optical density threshold.

14. The method of claim 11, comprising determining that light scattering by the fluid for electromagnetic radiation measured by the selected measurement channel is below a scattering threshold.

15. The method of claim 10, comprising using data from the spectrometer to identify the fluid of the well within the downhole tool as oil.

16. An apparatus comprising:
a downhole sampling tool including an intake configured to receive a formation fluid of a well within the downhole sampling tool and a downhole fluid analysis module having a spectrometer and configured to enable measurement of an optical density of the received formation fluid of the well; and a controller operable to determine asphaltene content of the received formation fluid of the well using the optical density of the received formation fluid of the well and a formation volume factor of the received formation fluid of the well and additional parameters that are derived from an analysis of optical spectra, formation volume factors, and asphaltene contents of previously sampled crude oils in a database, wherein the formation volume factor relates the optical density of the received formation fluid of the well to an optical density of a stock tank oil.

17. The apparatus of claim 16, wherein the controller is operable to determine the formation volume factor of the received formation fluid of the well.

18. The apparatus of claim 16, wherein the downhole fluid analysis module is configured to enable measurement of optical densities of the received formation fluid of the well to electromagnetic radiation of two different wavelengths and the controller is operable to determine the asphaltene content of the received formation fluid of the well based on the difference between the optical densities of the received formation fluid of the well for the two different wavelengths.

19. The apparatus of claim 16, wherein the downhole fluid analysis module is configured to enable measurement of the optical density of the received formation fluid of the well for infrared electromagnetic radiation and the controller is operable to determine the asphaltene content of the received formation fluid of the well using the optical density of the received formation fluid of the well for the infrared electromagnetic radiation.

20. The apparatus of claim 16, wherein the controller is provided within the downhole sampling tool.

* * * * *